United States Patent
Aramaki

(10) Patent No.: US 10,104,887 B2
(45) Date of Patent: Oct. 23, 2018

(54) METHOD FOR CONTROLLING AGRICULTURAL PESTS IN SUGAR CANE

(75) Inventor: Paulo Hiromitu Aramaki, São Paulo (BR)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 14/390,418

(22) PCT Filed: Apr. 4, 2012

(86) PCT No.: PCT/EP2012/056199
§ 371 (c)(1),
(2), (4) Date: Oct. 28, 2014

(87) PCT Pub. No.: WO2013/149658
PCT Pub. Date: Oct. 10, 2013

(65) Prior Publication Data
US 2015/0173350 A1    Jun. 25, 2015

(51) Int. Cl.
*A01N 25/00* (2006.01)
*A01N 25/14* (2006.01)
*A01N 43/88* (2006.01)

(52) U.S. Cl.
CPC ............. *A01N 25/14* (2013.01); *A01N 25/00* (2013.01); *A01N 43/88* (2013.01)

(58) Field of Classification Search
None
See application file for complete search history.

(56) References Cited

FOREIGN PATENT DOCUMENTS

| CN | 101999399 | * | 4/2011 | ............. A01N 25/12 |
| CN | 102379285 | * | 3/2012 | ............. A01N 25/14 |
| WO | 2011161071 A2 | | 12/2011 | |

OTHER PUBLICATIONS

Machine translation of CN 101999399, Obtained from <http://worldwide.espacenet.com>, Accessed Oct. 19, 2015.*
Dinardo-Miranda et al., Neotrop. Entomol. v.33 n. 1 Londrina Jan. / Feb. 2004.*
Machine translation of Dinardo-Miranda et al., Neotrop. Entomol. v.33 n. 1 Londrina Jan. / Feb. 2004. Translation by Google Translate. Accessed Oct. 19, 2015.*
Machine translation of CN 102379285, obtained from <https://worldwide.espacenet.com/>, Accessed Dec. 5, 2016.*
Database WPI, Week 201224, XP002690956, Sep. 14, 2011, Thomson Scientific, London, GB.
Database WPI, Week 201140, XP002690958, Apr. 6, 2011, Thomson Scientific, London, GB.
International Preliminary Report on Patentability dated Sep. 10, 2014 received in International Application No. PCT/EP2012/056199.
International Search Report dated Feb. 13, 2013 received in International Application No. PCT/EP2012/056199.
Submission to European Patent Office dated Feb. 3, 2014 in International Application No. PCT/EP2012/056199.
Submission to European Patent Office dated May 12, 2014 in International Application No. PCT/EP2012/056199.

* cited by examiner

*Primary Examiner* — Alicia L Otton

(57) ABSTRACT

The present invention relates to methods of controlling crop pests. In particular it relates to a method of applying pest control formulations without the use of water, wherein the pesticide is selected from the group comprised of thiamethoxam, imidacloprid, clothianidin, thiacloprid, fipronil, cyantraniliprole, chlorantraniliprole, or a mixture thereof, wherein the non-liquid pesticide formulation is applied between harvesting of the crop and spreading of mulch over the soil.

6 Claims, No Drawings

METHOD FOR CONTROLLING AGRICULTURAL PESTS IN SUGAR CANE

This application is a 371 filing of International Application No. PCT/EP2012/056199, filed Apr. 4, 2012, the contents of which are incorporated herein by reference.

The present invention relates to methods of controlling crop pests. In particular it relates to a method of applying pest control formulations without the use of water, wherein the pesticide is selected from the group comprised of thiamethoxam, imidacloprid, clothianidin, thiacloprid, fipronil, cyantraniliprole, chlorantraniliprole, or a mixture thereof.

Crop pests cause severe damage to agriculture, resulting in serious crop losses. In straw generating crops, such as sugarcane, the large amount of organic matter spread over the soil in the form of mulch after harvest promotes several pests, such as coleopterans, scales, termites, ants, leafhoppers, fungi, bacteria, nematodes and weeds if no preventive measure is taken.

In sugarcane plantations, after harvesting, which takes place in the dry season, the remaining stalk is left on the soil so that the plant re-buds and a new crop is grown. Sugarcane pests usually arise from their latent forms, such as eggs, larvae, spores, etc, after the first rains and attack the re-budding plants.

Sugarcane pests are usually controlled by burning the crop area before harvest. This practice, however is undesirable due to several factors, such as exposing the soil to the sun and rain, which loses nutrients, causing respiratory diseases in the population living nearby, and releasing ashes into the air, for example.

Sugar cane field burning is carried out before harvesting the cane to make the process easier and require less manual labor. It takes place during the harvest season, lasting from May to November (dry season) in the southeast, (Cannavam Rípoli et al., Scientia Agricola, vol. 57, n 4, 2000) with the peak of the burning season being in August. (Lara et al., Atmospheric Environment, vol. 39, n. 26, 2005) In the burning process, the field is set fire to and the leaves are burned off of the stalks. About 80% of the "trash" or mulch, including straw, the tops, and green and dry leaves, are burned off. These components constitute about 25% of the entire sugar cane stalk. The burning kills microorganisms and pests and burns the trash, both of which keep the soil rich when left in the fields. (Cannavam Rípoli et al., Scientia Agricola, vol. 57, n 4, 2000)

New technological advancements in sugarcane cultivation impose novel challenges upon pest control. The move towards mechanized harvesting and the prohibition of "trash" burning before or after harvest means that more mulch is left over the soil. This organic matter deposited on the soil maintains humidity and favors proliferation of pests and pathogens, coleopterans, scales, termites, ants, leafhoppers, fungi, bacteria, nematodes and weeds. (Marcondes J. E. M. et al., 2003).

Since the mulch covers the soil, it helps keeping humidity and protects it from the loss of nutrients. Pests' latent forms, however, are also preserved and usually arise after the first rains. An alternative to burning is the use of pesticides to control crop pests and protect the re-budding crop.

In order to make pesticides easy to use, optimize performance and increase stability in storage, pesticides are formulated with other inert ingredients. Common pesticide formulations can be dry sprayable formulations, liquid sprayable formulations and dry spreadable formulations.

Dry sprayable formulations can be Wettable powders (WP), Water dispersible granules (WG) and Soluble powder (SP).

Liquid sprayable formulations can be Soluble (liquid) concentrates (SL), Suspension concentrates (SC), Emulsifiable concentrates (EC), Microemulsions (ME), Oil dispersions and Capsule suspensions (CS).

Dry spreadable formulations can be granules (GR), dusts (DP) or microgranules (MG).

Pesticides such as Thiamethoxam, Imidacloprid, Clothianidin, Thiacloprid, Fipronil, Cyantraniliprole, Clorantraniliprole, or any one of the Neonicotinoid group usually formulated as liquid sprayable formulations, in order to be dissolved in a liquid solution and applied to the crop and crop area via spray. However, for the reasons described above, the spraying of liquid formulations, and/or formulations dissolved in water has several disadvantages.

An option to control sugarcane pests which reaches populational peaks after the first rain is the application of pesticides during the harvest, using a sprayer mounted in the mechanical harvester, so that the pesticide is applied to the soil under the mulch. This practice is known as a viable option to control insect pests, such as leafhoppers in sugarcane crop (Soares, W. R. O.; 2008 and Ferreira, H. J.; 2009).

This method, however, is not very effective, since the pesticide must be applied during the harvest in the dry season. Therefore, a pesticide formulation must be dissolved in water and loaded into a very large tank in order to be sprayed on the field. Due to being dissolved in water, the pesticide is sprayed in its active form, which means that it significantly loses activity over time, which means that its effect and, therefore, the crop protection is gradually lost over time.

In view of the above, the current methods of pest control with water soluble formulations impose several undesirable aspects, namely:

(i) a large amount of water, e.g. 50 to 300 l/ha is used in the process (ii) many travels are necessary to recharge the equipment;

(iii) a very heavy (about 500 kg) and expensive equipment is necessary;

(iv) the pesticide is not stable once sprayed in the field, resulting in a short period of protection.

Thus, there is a need for the provision of improved methods of controlling pests in crop areas wherein no water is used, a lighter and more inexpensive equipment is employed and wherein the active ingredient is kept stable after applied, preferably until the first rains, is of great interest to the art.

The present invention provides a surprising solution to the undesirable aspects of the prior art by providing a method for controlling agricultural pests, wherein the pesticide is applied directly to the raton cane on the soil during the harvest before straw is spread, with a small, light and inexpensive equipment easily attachable to the mechanical harvester, wherein no water is used and the active ingredient is kept stable until the first rain.

It has been surprisingly demonstrated that formulations prepared to be dissolved in water prior to spraying, can be applied directly to the soil simultaneously to the harvest, using a non-liquid formulation applying equipment adapted to small dosages of formulation applied per area, attached to the mechanical harvester. By using the non-liquid applying equipment, which is approximately 20 times lighter and 5 times more inexpensive than the liquid applying equipment the present method allows for the active ingredient, to remain stable until activated by water, usually rain, which also triggers the emergence of pests.

In a first embodiment, the invention provides a method of controlling crop pests comprising applying a non-liquid formulation, directly to the soil between harvesting of the crop and before the straw is spread over the field.

In another embodiment of the present invention, the non-liquid formulation is applied by a non-liquid formulation applying equipment attached to a mechanical harvester and the non-liquid formulation is applied simultaneously to the harvest.

In a more preferred embodiment, said non-liquid applying equipment is attached to the mechanical harvester in such a manner that the pesticide formulation is applied Non-liquid formulations will be understood by the skilled technician as Dry spreadable formulations, such as granules (GR), dusts (DP) or microgranules (MG) or dry sprayable formulations, such as wettable powders (WP), water dispersible granules (WG) and soluble powder (SP).

In a preferred embodiment, dry sprayable formulations are used. In an even more preferred embodiment, a dispersible granule (WG) formulation is used. The WG formulation optionally comprises, for example, anti-foaming, surfactants and emulsifying compounds, which help dissolving the formulation in water and dispersing, said dissolved formulation, at the crops or crop area.

In another preferred embodiment, the non-liquid formulation comprises 5% or more of active ingredient based on the weight of the formulation. More preferably the non-liquid formulation comprises 10% or more of active ingredient based on the weight of the formulation. Even more preferably the non-liquid formulation comprises 15% or more of active ingredient based on the weight of the formulation. Most preferably, the non-liquid formulation comprises 25% or more of active ingredient based on the weight of the formulation.

In another embodiment, the non-liquid formulation may be optionally mixed with clay granules before applying the formulation to the soil. The skilled technician will understand that clay granules will be used to dilute the formulation in order to accomplish the desired dosage per area. Therefore, the ratio of formulation to clay granules used will depend on the active ingredient weigh present in the formulation. Examples of clay granules are readily available to a skilled person from different suppliers for use in agrochemical products.

A pesticide or active ingredient is usually formulated into a composition which includes, in addition to the pesticide, a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that solid compositions (formulations) comprise, by weight, 3 to 50%, more preferably 5 to 40%, for example 10 to 30%, such as 15 to 30%, of an active ingredient.

The compositions can be chosen from a number of formulation types, including dustable powders (DP), soluble powders (SP), water soluble granules (SG), water dispersible granules (WG), wettable powders (WP), and granules (GR) (slow or fast release). The formulation type chosen in any instance will depend upon the particular purpose envisaged and the physical, chemical and biological properties of the active ingredient Dustable powders (DP) may be prepared by mixing an active ingredient with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing an active ingredient with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing an active ingredient with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of an active ingredient and one or more powdered solid diluents or carriers, or from pre-formed blank granules by absorbing an active ingredient (or a solution thereof, in a suitable agent) in a porous granular material (such as pumice, attapulgite clays, fuller's earth, kieselguhr, diatomaceous earths or ground corn cobs) or by adsorbing an active ingredient (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The compositions as a rule comprise 0.1 to 99%, in particular 0.1 to 95%, of the active ingredient and 1 to 99.9%, in particular 5 to 99.9%, of at least one solid auxiliary, it being possible as a rule for 0 to 25%, in particular 0.1 to 20%, of the composition to be surfactants (% is in each case per cent by weight). Preferred compositions are composed, in particular, as follows (%=per cent by weight):
Dusts:
combination: 0.1 to 10%, preferably 0.1 to 1%
solid carrier: 99.9 to 90%, preferably 99.9 to 99%
Wettable Powders:
combination: 0.5 to 90%, preferably 1 to 80%
surfactant: 0.5 to 20%, preferably 1 to 15%
solid carrier: balance
Granules:
combination: 0.5 to 60%, preferably 3 to 40%
solid carrier: 99.5 to 70%, preferably 97 to 85%

Examples of specific formulation examples for use in crop protection are given below (%=per cent by weight):

EXAMPLE F1

Granules

|  | a) | b) | c) | d) |
| --- | --- | --- | --- | --- |
| Active ingredient | 5% | 10% | 8% | 21% |
| Kaolin | 94% | — | 79% | 54% |
| Finely divided silicic acid | 1% | — | 13% | 7% |
| Attapulgite | — | 90% | — | 18% |

The macrocyclic lactone compound and chelating agent are dissolved in dichloromethane, the solution is sprayed onto the mixture of carriers and the solvent is evaporated under reduced pressure.

EXAMPLE F2

Wettable Powder

|  | a) | b) | c) |
| --- | --- | --- | --- |
| Active ingredient | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |

-continued

|  | a) | b) | c) |
| --- | --- | --- | --- |
| Octylphenol polyethylene glycol ether (7-8 mol of EO) | — | 2% | — |
| Finely divided silicic acid | 5% | 10% | 10% |
| Kaolin | 62% | 27% | — |

Macrocyclic lactone compound, chelating agent and additives are mixed and the mixture is ground in a suitable mill. This gives wettable powders which can be diluted with water to give suspensions of the desired concentration.

EXAMPLE F3

Extruder Granules

| Active ingredient | 60% |
| --- | --- |
| Sodium lignosulphonate | 10% |
| Carboxymethylcellulose | 1% |
| Kaolin | 29% |

Macrocyclic lactone compound, chelating agent and additives are mixed, the mixture is ground, moistened with water, extruded and granulated, and the granules are dried in a stream of air.

EXAMPLE F4

Coated Granules

| Active ingredient | 3% |
| --- | --- |
| Polyethylene glycol (MW 200) | 3% |
| Kaolin | 94% |

In a mixer, the finely ground macrocyclic lactone compound and chelating agent are applied uniformly to the kaolin which has been moistened with polyethylene glycol. This gives dust-free coated granules.

The composition may also comprise further solid adjuvants, preservatives, viscosity regulators, binders and/or tackifiers as well as fertilisers or other active ingredients for obtaining special effects, e.g., acaricides, bactericides, fungicides, nematicides, molluscicides or selective herbicides.

In an embodiment, independent of other embodiments, the non-liquid pesticide formulation comprises one or more surfactants (SFA), such as lignosulfonates, polyacrylates etc.

In an embodiment, independent of other embodiments, the non-liquid pesticide formulation comprises one or more soluble filler material, such as lactose, urea etc.

In an embodiment, independent of other embodiments, the non-liquid pesticide formulation does not comprise a surfactant (SFA) and/or soluble filler material.

Pesticides such as thiamethoxam, imidacloprid, clothianidin, thiacloprid, fipronil, cyantraniliprole, and chlorantraniliprole may be used in the present invention. In a preferred embodiment, the pesticide is thiamethoxam.

The skilled technician will understand that the present method may be applied to crops that leave mulch over the soil and/or that re-bud after harvest. More preferably, the crop is selected from sugarcane.

The present invention would also be applicable for use in sugar cane nurseries as well. The material harvested in the sugar cane nurseries is not sent to mills for sugar or ethanol production but rather kept for planting new fields. Therefore, the importance to have healthy cane seedlings by preventing the nurseries being attacked by the mentioned pests is also important.

In another embodiment of the invention, the non-liquid applying equipment, preferably a GR formulation applying equipment comprises a high precision electric dosimeter, capable of distributing small amount of the formulation.

In a more preferable embodiment, the non-liquid applying equipment comprises a high precision electric dosimeter capable of distributing 0.8 g of formulation/m (5.0 kg/ha) or less. In an even more preferred embodiment, the non-liquid applying equipment comprises a high precision electric dosimeter capable of distributing 0.4 g of product/m (2.5 kg/ha) or less. In a specially preferred embodiment, the non-liquid applying equipment comprises a high precision electric dosimeter capable of distributing 0.48 g of product/m (3 kg/ha) or less. In a most preferred embodiment, the non-liquid applying equipment comprises a high precision electric dosimeter capable of distributing 0.16 g of product/m (1.0 kg/ha) or less.

In another embodiment of the invention, the crop pest is an insect pest, such as, but not limited to, coleopterans, hemipterans and homopterans. More preferably the crop pest is selected from the group consisting of leafhoppers, scales and beetles. Most preferably, independent of any other embodiments, the crop pest is one or more selected from *Mahanarva fimbriolata, Sphenophorus levis* or *Saccharicoccus sacchari, Diatraea sacharallis* and *Elasmopalus lignosellus*.

It should be understood that modifications which do not substantially affect the activity of various forms of this invention are also included in the definition of the invention presented here. Therefore, the following examples are intended to illustrate but not limit the present invention.

EXAMPLE 1

*M. fimbriolata* is one of the most important sugarcane insect pest (J. E. M. Marcondes et al., 2003) and its control has been done primarily through mulch burning after harvest, which kills the remaining eggs. With the prohibition of mulch burning, the eggs are not killed and the mulch left in the field by the harvester further protects the insect's eggs from low humidity, high temperature and sprayed pesticides. Its first generation in the fields follows the first rain after harvest.

Thiamethoxam is currently used as a 250 g/kg WG formulation (Actara® 250 WG) to control sugarcane insect pests, however said formulation is diluted in water in order to be sprayed on the field in a ratio of 50 L/ha. The spraying equipment weights around 500 kg and the reservoir tank must be frequently recharged with pesticide dilution in order to spray large crop areas.

Since the WG formulation and thiamethoxam itself are very soluble in water, the active ingredient's activity and, therefore, the protecting effect are gradually lost when sprayed in a liquid solution, allowing the pest to overcome the protection over time. Hence, the protection of the re-budding plants from the attack of pests is limited to the duration of the active ingredient's activity after spared on the crop or crop site.

In view of these undesirable aspects of the prior art, thiamethoxam is currently applied after the emergence of the pest, which results in a high demand for the spraying equipment during the pest populational peak.

According to the method of the present invention, a non-liquid formulation applying equipment attached to the mechanical harvester is used to spread a non-liquid thiamethoxam formulation, preferably a WG formulation, optionally mixed with clay granules, over the soil after plants are harvested, but before mulch is spread over the field. Therefore, a simpler, lighter and more inexpensive non-liquid formulation spreading equipment, weighting around 15-30 kg can be employed, and the application may be done simultaneously to the harvest, since the formulation will remain stable until the first rains.

The method of the present invention was used to control the root froghopper, *Mahanarva fimbriolata* in sugarcane crop with a non-liquid thiamethoxam 250 g/kg WG formulation (25% AI concentration; known as Actara® 250 WG).

Table I below shows the results, in several sugarcane farms, of the different application regimes of a thiamethoxam 250 WG formulation—It shows the result for a liquid pesticide application of thiamethoxam 250 WG with water (TMX spray), compared with a non-liquid pesticide application: (i) thiamethoxam 250 WG formulation alone (TMX), and (ii) thiamethoxam 250 WG formulation mixture with clay (TMX & clay).

As can be seen from Table I, the method of the present invention is more efficient at protecting the crop against pests, in particular *Mahanarva fimbriolata*.

| Farm | Variety | Application Date | Evaluations *Mahanarva fimbriolata* on sugarcane plantation | | | | |
|---|---|---|---|---|---|---|---|
| | | | November | | | | December |
| | | | Control | TMX + clay | TMX | TMX Spray | Control |
| Saci/549 | RB85 5453 | 7 Jul. 2011 | 0.25 | 0.25 | 0.125 | 0 | 0.625 |
| Aliança/15 | RB86 7515 | 4 Aug. 2011 | 4.125 | 1.875 | 1.5 | 2.625 | 2.75 |
| Espraiado/23 | RB86 7515 | 10 Sep. 2011 | 5.75 | 2.75 | 2.875 | 5.6 | 0.625 |
| Fim da Picada/170 | RB72 454 | 11 Oct. 2011 | 10 | 2.5 | 5.5 | 2.75 | 1.125 |
| Barreirinho 2/501 | RB72 454 | 4 Nov. 2011 | 6.625 | 3.1 | 3.5 | 1.25 | 1.125 |
| Cachoeira/38 | SP81 3250 | 22 Jul. 2011 | 13.625 | 33.8 | 15.75 | 32 | 43 |
| Cachoeira/35 | SP81 3251 | 22 Jul. 2011 | 28.5 | 17.5 | 24.5 | 14.25 | 13 |
| Santa Cruz/03 | SP80 1816 | 20 Aug. 2011 | 14.25 | 21.5 | 11 | 28.75 | 9.5 |
| Santo Antonio II/27 | SP80 1816 | 15 Sep. 2011 | 4.25 | 1.85 | 0.35 | 8 | 0.25 |

-continued

| | | | | | | | |
|---|---|---|---|---|---|---|---|
| Vargem/18 | SP81 3250 | 18 Oct. 2011 | 1.5 | 1.5 | 2.3 | 1.25 | 0.5 |
| Santo Antonio/01 | SP80 1816 | 1 Nov. 2011 | 49 | 44.75 | 36.5 | 25.62 | 3.5 |
| Bloco2141/05 | RB86 7515 | 6 Jul. 2011 | 0.5 | 0 | 0 | 0 | 0.25 |
| São Gabriel 5588/56 | SP81 3250 | 21 Jul. 2011 | 2 | 0.25 | 0.12 | 0.5 | 1.25 |
| Bloco 4303/03 | RB86 7515 | 25 Aug. 2011 | 0.25 | 0 | 0 | 0 | 0.125 |
| Bloco 2353/01 | RB93 5744 | 6 Oct. 2011 | 1 | 0 | 0.25 | 1.12 | 1 |
| Durval Bradesg | SP87 365 | 21 Jun. 2011 | 5.5 | 0.875 | 0.875 | 1 | 19 |
| Branco Perez/quadra 1 | SP81 3250 | 5 Oct. 2011 | 0.25 | 0 | 0 | 0 | 2.5 |
| Sergio Popi/Quadra01 | RB86 7515 | 5 Oct. 2011 | 5.5 | 0.12 | 1 | 1.25 | 0.125 |
| Capão das Perobas/30 | SP81 3250 | 5 Aug. 2011 | 0 | 0 | 0 | 0 | 4.125 |
| Capão das Perobas/15 | RB82 3336 | 5 Aug. 2011 | 0 | 0 | 0 | 0 | 0.125 |
| Luiz Antonio/06 | RB85 5453 | 28 Jun. 2011 | 0 | 0 | 0 | 0 | 0.5 |
| Santa Maria da Rocha/02 | RB85 5453 | 9 Aug. 2011 | 0 | 0 | 0 | 0 | 0.125 |
| Santo Antonio/42 | RB85 5453 | 29 Sep. 2011 | 0 | 0 | 0 | 0 | 0.25 |
| São José/07 | SP80 1816 | 2 Sep. 2011 | 0 | 0 | 0 | 0 | 0.125 |
| Bonança/06 | RB93 5744 | 19 Sep. 2011 | 0 | 0 | 0 | 0 | 0 |
| Corrego Rico/89 | PO 8862 | 9 Nov. 2011 | 0 | 0 | 0 | 0 | 0 |
| Corrego Rico/62 | SP81 3250 | 9 Nov. 2011 | 0 | 0 | 0 | 0 | 0 |
| | | | 152.875 | 132.62 | 106.145 | 125.965 | 105.5 |

| | Evaluations *Mahanarva fimbriolata* on sugarcane plantation | | | | | | |
|---|---|---|---|---|---|---|---|
| | December | | | January | | | |
| Farm | TMX + clay | TMX | TMX Spray | Control | TMX + clay | TMX | TMX Spray |
| Saci/549 | 0.375 | 0.625 | 0.125 | 2.5 | 0.5 | 2 | 0.75 |
| Aliança/15 | 0.5 | 0.5 | 1 | 21 | 3.5 | 4 | 7 |
| Espraiado/23 | 0.125 | 0.5 | 0.5 | 17.5 | 3.5 | 2 | 16.75 |
| Fim da Picada/170 | 0.375 | 0.25 | 0.25 | 15.25 | 3.25 | 1.5 | 10.75 |
| Barreirinho 2/501 | 0.125 | 0.125 | 1 | 20.1 | 3.75 | 4 | 5.25 |
| Cachoeira/38 | 33.25 | 12.25 | 5.25 | 58.5 | 18.75 | 21.25 | 13.25 |
| Cachoeira/35 | 2 | 0.5 | 1 | 34.5 | 2 | 1 | 4.25 |
| Santa Cruz/03 | 0.75 | 2 | 0.5 | 8.5 | 13 | 11.5 | 3.5 |
| Santo Antonio II/27 | 0.25 | 0.25 | 0 | 23.5 | 3.5 | 0.25 | 24.25 |
| Vargem/18 | 0.25 | 0.25 | 0 | 16.25 | 1.75 | 3.75 | 2.25 |
| Santo Antonio/01 | 0.75 | 0.25 | 3.25 | 3 | 0.5 | 0.5 | 1.75 |
| Bloco2141/ 05 | 0 | 0 | 0 | 1 | 0 | 0 | 0 |
| São Gabriel 5588/56 | 0 | 0 | 0.125 | 7.75 | 0 | 0.25 | 0 |
| Bloco 4303/03 | 0 | 0 | 0 | 5 | 0 | 0 | 0.25 |
| Bloco 2353/01 | 0 | 0 | 0 | 1 | 0.5 | 0.25 | 0.5 |
| Durval Bradesg | 0.75 | 0.5 | 0.5 | 12.25 | 0.75 | 0.5 | 1 |
| Branco Perez/quadra 1 | 0 | 0 | 0 | 1 | 0 | 0.25 | 0.5 |
| Sergio Popi/Quadra01 | 0 | 0 | 0 | 0.5 | 0 | 0 | 0 |
| Capão das Perobas/30 | 0 | 0 | 0 | 2.75 | 0 | 0 | 0 |
| Capão das Perobas/15 | 0 | 0 | 0 | 0.5 | 0 | 0 | 0 |
| Luiz Antonio/06 | 0 | 0 | 0 | 0.125 | 0 | 0 | 0 |
| Santa Maria da Rocha/02 | 0 | 0 | 0 | 0 | 0 | 0 | 0 |
| Santo Antonio/42 | 0 | 0 | 0 | 0 | 0 | 0 | 0 |
| São José/07 | 0 | 0 | 0 | 4.25 | 1.25 | 0.25 | 1.375 |
| Bonança/06 | 0 | 0 | 0 | 0.125 | 0 | 0 | 0 |
| Corrego Rico/89 | 0 | 0 | 0 | 0.75 | 0 | 0 | 0.25 |
| Corrego Rico/62 | 0 | 0 | 0 | 2.25 | 0 | 0 | 0 |
| | 39.5 | 18 | 13.5 | 259.85 | 56.5 | 53.25 | 93.625 |

The invention claimed is:

1. A method of controlling Mahanarva fimbriolata in sugar cane, said method comprising:
   applying a non-liquid pesticide formulation to soil in which the sugar cane grows between harvesting of the sugar cane and spreading of mulch over the soil, wherein
   the non-liquid pesticide formulation comprises, as an active ingredient, thiamethoxam;
   the active ingredient (i) is at least 25 weight %, based on a total weight of the non-liquid pesticide formulation; and
   the non-liquid pesticide formulation is mixed with clay granules before being applied to the soil.

2. The method according to claim 1, wherein the pesticide formulation is applied to the soil in such a manner that the pesticide formulation is applied simultaneously during harvesting of the sugar cane and before mulch is spread over the soil.

3. The method according to claim 2, wherein a device for applying the non-liquid pesticide formulation is attached to a mechanical harvester.

4. A method according to claim 1, wherein the non-liquid pesticide formulation is in a form of a wettable granule (WG).

5. A method of applying a non-liquid formulation to a sugarcane field, said method comprising:
   applying a non-liquid formulation selected from granules (GR), dust (DP), microgranules (MG), wettable powders (WP), water dispersible granules (WG) and soluble powder (SP) to a sugarcane field, wherein:
   the non-liquid formulation comprises, as an active ingredient, thiamethoxam in an amount of at least 25 weight percent (wt %) based on a total weight of the non-liquid formulation;
   the non-liquid formulation is applied to soil of the sugarcane field simultaneously during harvest of sugarcane within the sugarcane field and before mulch is spread over the sugarcane field;
   the non-liquid formulation is applied to the soil of the sugarcane field by a device that is attached to a mechanical harvester of the sugarcane; and
   about 5.0 kg/ha or less of the non-liquid formulation is applied to the sugarcane field by the device.

6. A method according to claim 5, wherein the non-liquid formulation is a water dispersible granules (WG).

\* \* \* \* \*